US009056921B2

(12) United States Patent
Andersen et al.

(10) Patent No.: US 9,056,921 B2
(45) Date of Patent: Jun. 16, 2015

(54) METHOD FOR MAKING MATURE INSULIN POLYPEPTIDES

(75) Inventors: Asser Sloth Andersen, Herlev (DK); Lars Hojlund Christensen, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 1697 days.

(21) Appl. No.: 12/063,692

(22) PCT Filed: Aug. 15, 2006

(86) PCT No.: PCT/EP2006/065303
§ 371 (c)(1),
(2), (4) Date: Apr. 7, 2010

(87) PCT Pub. No.: WO2007/020256
PCT Pub. Date: Feb. 22, 2007

(65) Prior Publication Data
US 2011/0111460 A1    May 12, 2011

Related U.S. Application Data

(60) Provisional application No. 60/724,640, filed on Oct. 7, 2005.

(30) Foreign Application Priority Data

Aug. 16, 2005   (EP) ..................................... 05107513

(51) Int. Cl.
| C12N 1/19 | (2006.01) |
| C12N 15/17 | (2006.01) |
| C12N 15/63 | (2006.01) |
| C12N 1/16 | (2006.01) |
| C07K 14/62 | (2006.01) |

(52) U.S. Cl.
CPC ................ *C07K 14/62* (2013.01); *C12N 15/63* (2013.01); *C12N 1/16* (2013.01)

(58) Field of Classification Search
None
See application file for complete search history.

(56) References Cited

U.S. PATENT DOCUMENTS

| 4,914,026 A | 4/1990 | Brake et al. |
| 5,716,927 A * | 2/1998 | Balschmidt et al. ............ 514/6.1 |
| 6,337,194 B1 * | 1/2002 | Hadfield et al. ............. 435/69.7 |
| 6,348,327 B1 | 2/2002 | Gorman et al. |
| 8,153,395 B2 | 4/2012 | Norgaard |
| 2003/0104981 A1 | 6/2003 | Mandic |

FOREIGN PATENT DOCUMENTS

| EP | 0163529 | 12/1985 |
| WO | WO 90/01038 | 2/1990 |
| WO | WO 90/10075 | 9/1990 |
| WO | WO 90/12814 | 11/1990 |
| WO | WO 95/02059 | 1/1995 |
| WO | 95/35384 A1 | 12/1995 |
| WO | WO 97/03089 | 1/1997 |
| WO | WO 01/49870 | 7/2001 |
| WO | WO 02/079250 | 10/2002 |
| WO | 2007/020256 A1 | 2/2007 |
| WO | 2008/037735 A1 | 4/2008 |

OTHER PUBLICATIONS

Weiss et al. J. Biol. Chem. 276(43): 40018-40024, 2001.*
Kjeldsen et al., Journal of Biological Chemistry, "Engineering-Enhanced Protein Secretory Expression in Yeast With Application to Insulin", 2002, vol. 277, No. 21, pp. 18245-18248.
Kristensen et al., Journal of Biological Chemistry, "Alanine Scanning Mutagenesis of Insulin", 1997, vol. 272, No. 20, pp. 12978-12983.
Chu, Y-C et al., "The A14 Position of Insulin Tolerates Considerable Structural Alterations with Modest Effects on the Biological Behavior of the Hormone", Journal of Protein Chemistry, vol. 11, No. 5, 1992, pp. 571-577.
Frank, B.H. et al., "The Production of Human Proinsulin and its Transformation to Human Insulin and C-Peptide", Proceedings of the Seventh American Peptide Symposium, 1981, pp. 729-738.
Olsen, H.B. et al., "The Relationship Between Insulin Bioactivity and Structure in the $NH_2$-terminal A-chain Helix", J. Mol. Biol., 1998, vol. 284, No. 2, pp. 477-488.
Thim, L. et al., "Secretion of Human Insulin by a Transformed Yeast Cell", FEBS Letters, 1987, vol. 212, No. 2, pp. 307-312.
Thim, L. et al., "Secretion and Processing of Insulin Precursors in Yeast", Proc. Natl. Acad. Sci., USA, 1986, vol. 83, pp. 6766-6770.
Weiss et al, Journal of Biological Chemistry, "Activities of Monomeric Insulin Analogs at Position A8 Are Uncorrelated With Their Thermodynamic Stabilities", 2001, vol. 276, No. 43, pp. 40018-40024.
Bevan, Alison et al, Proceedings of the National Academy of Sciences of the USA, "Quantitative Assessment of Enzyme Specificity In Vivo: P2 Recognition by KEX2 Protease Defined in a Genetic System", 1998, vol. 95, No. 18, pp. 10384-10389.
Frank, Pettee, Zimmerman and Burck, Rich, Gross, Pierce Chemical Company. Rockford Illinois, "The Production of Human Proinsulin and Its Transformation to Human Insulin and C-Peptides", 1981,pp. 729-738.
Hopkins B D et al, Methods in Enzymology, "Introduction of KEX2 Cleavage Sites in Fusion Protein . . . ", 2000, vol. 327, pp. 107-118.
Hunt, S M N et al, Cytotechnology, "Processing of Mutated Human Proinsulin to Mature Insulin in the Non-Endocrine Cell Line, CHO", 1996, vol. 21, pp. 279-288.
Kjeldsen, Applied Microbiology and Biotechnology, Springer Verlag, DE, "Yeast Secretory Expression of Insulin Precursors", 2000, vol. 54, No. 3, pp. 277-286.

(Continued)

*Primary Examiner* — Christine J Saoud
(74) *Attorney, Agent, or Firm* — Nonna G. Akopyan; Reza Green; Richard W. Bork

(57) ABSTRACT

The invention is related to a method for making human insulin analogs by culturing an fungi cell comprising a DNA vector encoding a precursor for human insulin analog, wherein the said precursor comprises a connecting peptide flanked with cleavage sites at both junctions with the A- and the B-chain of the insulin peptide, respectively said cleavage sites being cleaved within the fungi cell allowing the cell to secrete high amount of correctly processed, mature two chain human insulin analog to the culture media.

16 Claims, 2 Drawing Sheets

(56) References Cited

OTHER PUBLICATIONS

Rockwell, Nathan C et al, Biochemistry, "Interplay Between S1 and S4 Subsites in KEX2 Protease: KEX2 Exhibits Dual Specificity for the P4 Side Chain", 1998, vol. 37, No. 10, pp. 3386-3391.

Todd R. Graham et al., Compartmental Organization of Golgi-Specific Protein Modification and Vacuolar Protein Sorting Events Defined in a Yeast SEC18 (NSF) Mutant, The Journal of Cell Biology. vol. 114(2), pp. 207-218 (1991).

Groskreutz DJ et al. Journal of Biological Chemistry. "Genetically Engineered Proinsulin Constitutively Processed and Secreted as Mature, Active Insulin." 1994. vol. 269(8). pp. 6241-6245.

Yanagita M et al. FEBS. "Processing of Mutated Proinsulin With Tetrabasic Cleavage Sites to Bioactive Insulin in the Non-Endocrine Cell Line." 1992. vol. 311(1). pp. 55-59.

Jonasson P et al. European Journal of Biochemistry. "Single-Step Trypsin Cleavage of a Fusion Protein to Obtain Human Insulin and Its C Peptide." 1996. vol. 236(2). pp. 656-661.

\* cited by examiner

METHOD FOR MAKING MATURE INSULIN POLYPEPTIDES

CROSS-REFERENCE TO RELATED APPLICATIONS

This application is a 35 U.S.C. §371 national stage application of International Patent Application PCT/EP2006/065303 (published as WO 2007/020256 A1), filed Aug. 15, 2006, which claimed priority of European Patent Application 05107513.3, filed Aug. 16, 2005; this application further claims priority under 35 U.S.C. §119 of U.S. Provisional Application 60/724,640, filed Oct. 7, 2005.

FIELD OF THE INVENTION

The present invention is related to a process for making mature human insulin analogues in yeast.

BACKGROUND OF THE INVENTION

Insulin is a polypeptide hormone produced in the beta cells of the islets of Langerhans. The active insulin molecule is a two-chain molecule consisting of a B- and an A-Chain connected by two disulphide bridges. The insulin is synthesized as a precursor molecule proinsulin with the structure B-C-A wherein the C-peptide chain connects the C-terminal amino acid residue in the B-chain with the N-terminal amino acid residue in the A-chain. Mature two-chain insulin is formed by cleavage of the C-peptide at the pair of basic amino acid residues situated at the junctions with the A- and B-chain. The A- and B-chain are held together by two disulphide bridges between the A7 and B7 and the A20 and B19 Cys residues, respectively. In addition, the biologically active insulin molecule has an internal disulphide bridge between the Cys residues in the position A6 and A11.

After the development of recombinant DNA technology numerous methods have been described to produce insulin and precursors thereof in genetically modified host cells. Thus methods for making insulin from *E. coli* are disclosed in e.g Frank, B. H., Pettee, J. M., Zimmerman, R. E. & Burck, P. J. In: Peptides. Synthesis-Structure-Function. Proceedings of the Seventh American Peptide Symposium (D. H. Rich and E. Gross, eds). Pierce Chemical Company, p. 729 (1981). As *E. coli* does not have the cellular machinery for folding the expressed polypeptide and establish the disulphide bridges connecting the A- and B chain in the mature insulin this strategy includes a number of in vitro processing steps such as in vitro establishment of the disulphide bridges during refolding and subsequent cleavage of the C-peptide.

In contrast to *E. coli* eukaryotes contain the necessary machinery for folding and establishing disulphide bridges and thus would seem to be good candidates for production of mature insulin in genetically modified organisms. U.S. Pat. No. 4,914,026 discloses a process for making mature insulin in yeast by insertion of the human proinsulin gene linked to the yeast α-factor leader sequence in a yeast host cell and growing the transformed yeast cell in a nutrient medium under conditions whereby proinsulin is expressed and secreted in mature form.

Thim et al, Proc Natl. Acad. Sci. USA, volume 83, 6766-6770 discloses expression of human proinsulin and a number of insulin precursors with a modified C-peptide such as RRE-AENLQKR (SEEQ ID NO:1), RREAPLQKR (SEQ ID NO:2), RREALQKR (SEQ IDNO:3), KREALQKR (SEQ ID NO:4) and RRLQKR (SEQ ID NO:5). SEQ ID NO:5 is also disclosed by Thim et al, in FEBS Letters, volume 212, number 2, 307-312.

Furthermore, WO 97/03089 disclosed expression of insulin precursors with the formula BZA wherein B and A are the A and B peptide chains of human insulin being linked by at least one disulphide bond and Z is a polypeptide comprising at least one proteolytic cleavage site, e.g. KREQKLISEE-ALVDKR (SEQ ID NO:6).

However, the disclosed insulin precursors only give rise to minute amounts of secreted mature insulin in the culture medium.

European patent application, 0163529A, PCT patent applications Nos. WO 95/02059 and WO 90/10075 disclose processes for making insulin and insulin analogues based on expression of a precursor of the insulin or insulin analogue in yeast that following initial recovery from the fermentation broth are enzymatically converted to the mature insulin or insulin analogue. The precursor molecules comprise certain modified C-peptides and may furthermore comprise an N-terminal extension of the insulin B-chain. The modified C-peptide and the possible N-terminal extension of the B-peptide are designed not to be cleaved in the yeast cell and thus the precursors are secreted as single chain peptides wherein the A- and the B-chain are still connected by the modified C-peptide but with correctly positioned disulphide bridges. The mature insulin or insulin analogue product is then obtained by a number of subsequent in vitro enzymatic steps to cleave the C-peptide and possibly the N-terminal extension. These enzymatic steps are time consuming, often costly and introduce additional impurities that subsequently have to be removed in further downstream process steps like expensive chromatography steps and the like.

A process for making mature insulin in genetically engineered animal cells that are not naturally capable of forming secretory granules is disclosed in U.S. Pat. No. 6,348,327.

The purpose of the present invention is to develop a fungi strain capable of secreting fully processed mature human insulin analogues so that expensive and time consuming downstream purification process steps are avoided.

SUMMARY OF THE INVENTION

In one aspect the invention is related to a method for making mature human insulin analogues by culturing an fungi cell comprising a DNA vector encoding a precursor for a human insulin analogue, wherein the said precursor comprises a connecting peptide flanked with cleavage sites at both junctions to the A- and the B-chain of the insulin peptide, respectively, said cleavage sites being cleaved within the fungi cell allowing the cell to secrete the correctly processed mature, two chain human insulin analogue to the culture media.

The human insulin analogues according to the present invention will be expressed as single chain precursors within the fungi cell and will be cleaved within the cell and secreted as mature, two chain human insulin analogues without the necessity of further in vitro processing.

The cleavage sites at each junction of the connecting peptide with the A- and B-chains of the insulin molecule may be the same or different but will typically be the same and in one embodiment the cleavage sites at the junctions to the A and to the B-chain are both Kex2 cleavage sites.

In another embodiment the cleavage sites are Yps1 sites.

The connecting peptide will have an amino acid composition which is optimized to ensure cleavage within the fungi cell to secrete the correctly maturated insulin analogue polypeptide.

In one embodiment of the invention the amino acid residue in the position penultimate to the cleavage site adjacent to the A-chain is selected from the group consisting of Phe, Leu, Ile, Tyr, Trp, Val, Met and Ala.

In another embodiment of the invention the connecting peptide will comprise a Leu, Ile, Tyr, Arg, Lys, His, Pro, Phe, Tyr, Trp, Met, Val or Ala amino acid residue in the position penultimate to the cleavage site adjacent to the A-chain.

In a further embodiment of the invention the connecting peptide will comprise a Leu or an Ile amino acid residue in this position.

We have also discovered that the amino acid residue in the same position should not be Asp, Glu or Gly.

The size of the C-peptide in human insulin is of 35 amino acid residues. Thus in one aspect of the present invention the connecting peptide will be of about the same length as the natural C-peptide.

In one embodiment the connecting peptide will be 2-35, 2-34, 2-33, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4 or 2-3 amino acid residues.

In a further embodiment the connecting peptide will be 3-35, 3-34, 3-33, 3-31, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5 or 3-4 amino acid residues.

In a further embodiment the connecting peptide will consist of 2, 3, 4, 5, 6, 7, 8, 9, 10, 11, 12, 13, 14, 15, 16, 17, 18, 19, 20, 21, 22, 23, 24, 25, 26, 27, 28, 29, 30 31, 32, 33, 34 or 35 amino acid residues.

The fungi cell will secrete high amounts of correctly processed human insulin analogues and in one embodiment the fungi cell is capable of secreting at least about 20 to about 50 mg/liter correctly processed mature, two chain human insulin analogue to the culture media.

In another embodiment the fungi cell is capable of secreting at least about 20 to about 80 mg/liter correctly processed mature, two chain human insulin analogue to the culture media.

In still another embodiment the fungi cell is capable of secreting at least about 100 mg/liter correctly processed mature, two chain human insulin analogue to the culture media.

The more efficient the cleavage of the connecting peptide from the insulin analogue precursor molecule is, the higher the final yield of the target protein is. Thus it is desirable that the amino acid composition of the connecting peptide enables an efficient cleavage of the cleavage sites at the junctions with the A- and B-chain, respectively.

In one embodiment of the invention at least 50% of the expressed single-chain insulin precursor molecule is cleaved to the mature two-chain molecule.

In another embodiment at least 60% of the expressed single-chain insulin precursor molecule is cleaved to the mature two-chain molecule.

In a still further embodiment at least 70% of the expressed single-chain insulin precursor molecule is cleaved to the mature two-chain molecule.

In a still further embodiment at least 75% of the expressed single-chain insulin precursor molecule is cleaved to the mature two-chain molecule.

In a still further embodiment at least 85% or at least 95% of the expressed single-chain insulin precursor molecule is cleaved to the mature two-chain molecule.

The fungi cell can be any fungi cell capable of expressing and secreting the maturated insulin analogues. However, yeast has turned out to be well suited for the present purpose, in particular *S. cerevisiae*.

The human insulin molecule has three helix structures one in the B-chain and two in the A-chain. The A-chain comprises two helical segments A2-A8 and A13-A19 joined by a loop in position A9-A11 and in the T-state conformation of insulin residues B9-B19 form the central a-helix of the B-chain. It has been shown that certain mutations in the insulin molecule will enhance the stability of these helix structure leading to a high biological activity (see N: Kaarsholm et. Al., Biochemistry 1993, 32, 10773-10778). The insulin analogues prepared by the present method will typically comprise mutations which may have a stabilising effect of the helix structure of the human insulin analogue molecule leading to secretion of higher yields.

Thus, in one embodiment the insulin analogues produced by the method according to the invention will comprise mutations in the insulin molecule in one or more of the positions A8, B10 and A14 and in a further embodiment the natural amino acid residues in these positions may be mutated with amino acid residues selected from the group consisting of Asp, Glu, His, Gln and Arg.

Further mutations of the insulin molecule includes mutations in the B28 and B29 position, mutation in the A18 position, deletions of the B30 or B1 amino acid residue and mutation of the A21 amino acid residue.

In one embodiment of the invention the amino acid residue in position B28 is Asp and the amino acid residue in position B29 is Lys.

In another embodiment of the invention the amino acid residue in position B28 is Lys, the amino acid residue in position B29 is Pro and the amino acid residue in position B30 is Thr.

In a further embodiment of the invention the amino acid in position A18 is Gln.

In a further embodiment of the invention the amino acid residue in position A21 is Gly.

In another embodiment of the invention the amino acid residue in position B10 is Glu.

In another embodiment of the invention the amino acid residue in position A8 is His.

In another embodiment of the invention the amino acid residue in position A14 is Glu.

In a still further embodiment of the invention the amino acid residue in position B10 is Glu, the amino acid residue in position A8 is His and the amino acid residue in position A14 is Glu.

In a still further embodiment of the invention the amino acid residue in the position B30 is deleted.

In one embodiment the human insulin precursor analogue has the amino acid sequence

B(1-30)-X-X-Z-Y-Y-A(1-21)

where B(1-30) is the B-chain of human insulin or an analogue thereof, A(1-21) is the human insulin A-chain or an analogue thereof, each X and each Y independently of each other are Lys or Arg or a Yps1 site and Z is a peptide sequence with from 1 to about 35 amino acid residues, with the proviso that at least one of the natural amino acid residues in the human insulin A- and/or the B-chain is mutated to another amino acid residue.

In one embodiment the sequences X-X and Y-Y are both Lys-Arg.

In another embodiment the sequences X-X and Y-Y are both Arg-Arg, Lys-Lys or Arg-Lys.

In a still further embodiment X-X is Lys-Arg and Y-Y is Arg-Arg or X-X is Arg-Arg and Y-Y is Lys-Arg.

In one embodiment Z is of the size 2-35, 2-34, 2-33, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4 or 2-3 amino acid residues.

In a further embodiment Z is of the size 3-35, 3-34, 3-33, 3-31, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5 or 3-4 amino acid residues.

In one embodiment of the invention Z may be of the size from 2, 3, 4, 5, 7, 7, 8, 9, 10, 11, 12, 13, 14, 15, 16, 17, 18, 19, 20, 21, 22, 23, 24, 25, 26, 27, 28, 29, 30 31, 32, 33, 34 and 35 amino acid residues.

In another embodiment of the invention Z is an amino acid sequence of 3-20 amino acid residues.

In another embodiment of the invention Z is an amino acid sequence of 3-19 amino acid residues.

In another embodiment of the invention Z is an amino acid sequence of 3-18 amino acid residues.

In another embodiment of the invention Z is an amino acid sequence of 3-15 amino acid residues.

In another embodiment of the invention Z is an amino acid sequence of 3-14 amino acid residues.

In another embodiment of the invention Z is an amino acid sequence of 3-13 amino acid residues.

In another embodiment of the invention Z is an amino acid sequence of 3-12 amino acid residues.

In another embodiment of the invention Z is an amino acid sequence of 3-11 amino acid residues.

In another embodiment of the invention Z is an amino acid sequence of 3-10 amino acid residues.

In another embodiment of the invention Z is an amino acid sequence of 3-9 amino acid residues.

In another embodiment of the invention Z is an amino acid sequence of 3-8 amino acid residues.

In another embodiment of the invention Z is an amino acid sequence of 3-7 amino acid residues.

In another embodiment of the invention Z is an amino acid sequence of 3-6 amino acid residues.

In another embodiment of the invention Z is an amino acid sequence of 3-5 amino acid residues.

In another embodiment of the invention Z is an amino acid sequence of 3-4 amino acid residues.

In one embodiment of the invention the amino acid residue in the position penultimate to the cleavage site Y-Y is selected from the group consisting of Leu, Ile, Tyr, Arg, Lys, His, Pro, Phe, Trp, Val, Met and Ala In one embodiment of the invention the amino acid residue in the position penultimate to the cleavage site Y-Y is Leu.

In one embodiment of the invention the amino acid residue in the position penultimate to the cleavage site Y-Y is Ile.

In one embodiment of the invention the amino acid residue in the position penultimate to the cleavage site Y-Y is Tyr.

In one embodiment of the invention the amino acid residue in the position penultimate to the cleavage site Y-Y is Arg.

In one embodiment of the invention the amino acid residue in the position penultimate to the cleavage site Y-Y is Lys.

In one embodiment of the invention the amino acid residue in the position penultimate to the cleavage site Y-Y is His.

In one embodiment of the invention the amino acid residue in the position penultimate to the cleavage site Y-Y is Pro.

In one embodiment of the invention the amino acid residue in the position penultimate to the cleavage site Y-Y is Phe.

In one embodiment of the invention the amino acid residue in the position penultimate to the cleavage site Y-Y is Trp.

In one embodiment of the invention the amino acid residue in the position penultimate to the cleavage site Y-Y is Met.

In one embodiment of the invention the amino acid residue in the position penultimate to the cleavage site Y-Y is Val.

In one embodiment of the invention the amino acid residue in the position penultimate to the cleavage site Y-Y is Ala.

In one embodiment of the invention Z has the sequence AspGlyLeuGly (SEQ ID No:7).

The remaining Z's may be any codable amino acid residues, which may be the same or different. However, in one embodiment the amino acid residue in Z in the position penultimate to the cleavage site Y-Y is not Asp, Glu or Gly.

In another aspect the invention is related to a DNA sequence encoding a human insulin analogue precursor comprising a connecting peptide which is designed to enable efficient cleavage of the cleavage sites within a fungi cell allowing the cell to secrete correctly processed mature, two chain human insulin analogue to the culture media.

In another aspect the invention is related to an expression vector comprising a DNA sequence encoding a human insulin analogue precursor comprising a connecting peptide which is designed to enable efficient cleavage of the cleavage sites within a fungi cell allowing the cell to secrete correctly processed mature, two chain human insulin analogue to the culture media.

In a further aspect the present invention is related to a transformed fungi cell comprising an expression vector comprising a DNA sequence encoding an human insulin analogue precursor comprising a connecting peptide which is designed to enable efficient cleavage of the cleavage sites within a fungi cell allowing the cell to secrete correctly processed mature two chain human insulin analogue to the culture media.

The human insulin analogues produced by the method according to the present invention may be used in the treatment of states which are sensitive to insulin. Thus, they can be used in the treatment of type 1 diabetes, type 2 diabetes and hyperglycaemia for example as sometimes seen in seriously injured persons and persons who have undergone major surgery.

Where expedient, the insulin analogues may be used in mixture with other types of insulin, e.g. insulin analogues with a more rapid onset of action. Examples of such insulin analogues are described e.g. in the European patent applications having the publication Nos. EP 214826, EP 375437 and EP 383472.

In a further aspect the present invention is related to pharmaceutical formulations comprising the human insulin analogues in combination with suitable pharmaceutically acceptable adjuvants and additives such as one or more agents suitable for stabilization, preservation or isotonicity.

DETAILED DESCRIPTION OF THE INVENTION

Figures 1, 2:
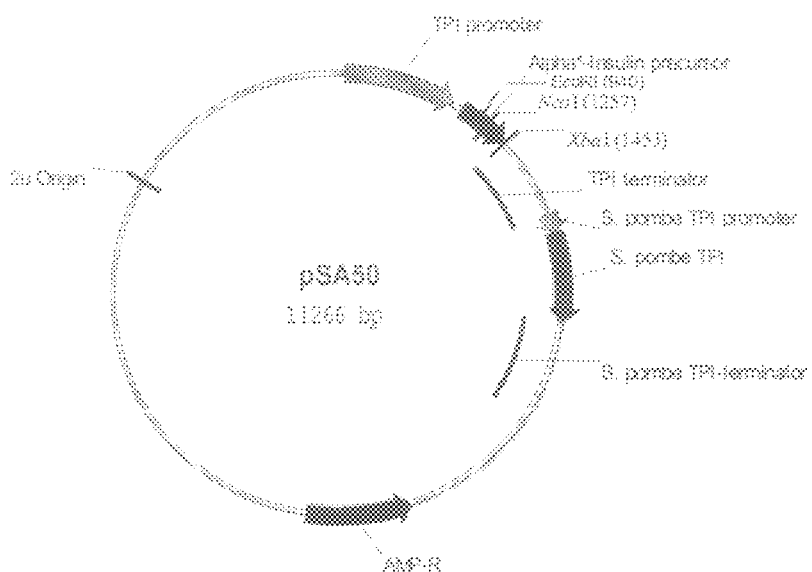
FIG. 1 shows an example of a yeast plasmid called pSA50. The plasmid contains an expression cassette comprising an EcoRI-XbaI fragment inserted into the plasmid between the transcription-promoter and the transcription-terminator of the *S. cerevisiae* TPI gene.
FIG. 2 shows the NcoI-XbaI DNA fragment containing the insulin precursor B(1-30)-KRDGLGKR-(A1-21), A18Q (SEQ ID NO:8) and the corresponding amino acid sequence (SEQ ID NO. 10) described in example 3.

Production of insulin by secretion of the mature product directly to the fermentation broth requires intracellular processing of insulin precursors comprising a connecting peptide flanked by a cleavage site at each ends. Such connecting peptide may be of the type B-KR(W)$_n$KR-A where B is the B-chain of human insulin and W is a peptide chain of varying length. The intracellular processing is facilitated by the Golgi proteases Kex1 and Kex2. The cleavage is a multiple step process where Kex2 in the first step will cleave at the KR sequence attached to the A-chain and convert the single-chain molecule to a two-chain molecule. Then Kex2 will cleave off the connecting peptide W to give a two-chain intermediate insulin molecule wherein the dipeptide KR is still connected to the C-terminal amino acid in the B-chain. Finally Kex1 will remove the last KR peptide sequence giving the mature, two-chain molecule.

Experiments have shown that efficient cleavage of the cleavage site at the A chain juncture is important for the further progress of the cleavage process and the connecting peptide according to the present invention is designed to enable an efficient in vivo cleavage of the cleavage site at the A-chain Kex2 leading to high yields of a secreted two-chain insulin molecule without the necessity of additional in vitro processing steps.

The secretion of high amounts of active mature, two-chain human insulin analogue from the yeast will significantly reduce the number of down stream purification steps necessary to produce a human insulin analogue of a purity sufficiently high for pharmaceutical purposes. Thus, in the method for making insulin in yeast disclosed in U.S. Pat. No. 4,916,212 an insulin precursor is converted into human insulin in two steps i.e. a transpeptidation to convert the single chain insulin precursor B(1-29)-Alal-Ala-Lys-A(1-21) into an ester of human insulin and then a hydrolysis of the insulin ester into human insulin. Each conversion step will require an initial separation step and at least one subsequent purification step. Thus at least six additional steps are necessary to produce the mature, two chain insulin including at least one enzymatic conversion.

It is well known that no enzymatic cleavage runs to a 100% cleavage leaving impurities of uncleaved or partially cleaved impurities which have to be efficiently removed in the case of pharmaceutical products. Thus, each cleavage step will be followed by at least one isolation or purification step, typically a chromatographic purification by means of exchange chromatography, gel filtration chromatography, affinity chromatography, or the like. Chromatographic column material for use in commercial scale is very expensive and therefore reduction of the number of such chromatographic steps has a significant impact on the production economy. A reduction of the downstream conversion and purification step will in addition reduce the amount of labor work and hours spent in the process and thus further improve the production economy.

In the present process where the mature, two chain insulin analogue can be isolated in high yields directly from the culture broth much fewer down stream process steps are necessary to produce a product of sufficient purity for pharmaceutical use.

The insulin analogues produced by the method according to the present invention may be modified in certain positions in the A- and or B-chain in addition to the modifications stabilizing the helix structures in the insulin molecule. Thus the amino acid residue in position B28 may be Asp. In another group of insulin analogues, the amino acid residue at position B1 has been deleted. A specific example from this group of insulin analogues is desB1 human insulin.

In another group of insulin analogues, the amino acid residue at position B30 has been deleted. In another group of insulin analogues, the amino acid residue at position B28 is Lys and the amino acid residue at position B29 is Pro.

In another group of insulin analogues the amino acid in position A18 may be Gln and in a still further embodiment the amino acid residue in position A21 may be Gly.

The DNA sequence encoding the insulin precursor analogues may be of genomic or cDNA origin, for instance be obtained by preparing a genomic or cDNA library and screening for DNA sequences coding for all or part of the polypeptide by hybridization using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the insulin precursore may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the insulin precursor is operably linked to additional segments required for transcription of the DNA, such as a promoter. The promoter may be any DNA sequence which shows transcriptional activity in the host cell of choice and may be derived from genes encoding proteins either homologous or heterologous to the host cell.

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

The DNA sequence encoding the insulin precursor may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

To direct the insulin into the secretory pathway of the host cells, a secretory signal sequence (also known as a leader sequence, prepro sequence or pre sequence) may be provided in the recombinant vector. The secretory signal sequence is joined to the DNA sequence encoding the insulin precursor in the correct reading frame. Secretory signal sequences are commonly positioned 5' to the DNA sequence encoding the peptide. The signal peptide may be naturally occurring signal peptide, or a functional part thereof, or it may be a synthetic peptide.

For efficient secretion in yeast, a sequence encoding a leader peptide may also be inserted downstream of the signal sequence and upstream of the DNA sequence encoding the insulin precursor.

The yeast host cell into which the DNA sequence or the recombinant vector is introduced may be any yeast cell which is capable of expressing the insulin precursor and includes *Saccharomyces* spp. or *Schizosaccharomyces* spp., in particular strains of *Saccharomyces cerevisiae* or *Saccharomyces kluyveri*. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882, 279).

Methods for transforming yeast cells with heterologous DNA and producing heterologous poly-peptides there from are described, e.g. in U.S. Pat. No. 4,599,311, U.S. Pat. No. 4,931,373, U.S. Pat. Nos. 4,870,008, 5,037,743, and U.S. Pat. No. 4,845,075. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373.

The process according to the present invention is a so called fermentation process. The fermentation is preferably carried out in aseptic, stirred tanks with supply lines for addition of compressed, sterile gasses consisting of but not limited to air, oxygen and ammonia. A fermentation tank can contain devices/sensors for monitoring pH, temperature, pressure, agitation rate, dissolved oxygen level, liquid content, foam level, feed addition rates and rates of adding acid and base.

The temperature may be within the range from about 25 to about 35, from about 26 to about 31, or from about 26 to about 29° C. The pH will be in the range of from about 4.0 to about 6.8 or from about 5.0 to about 6.5.

Agitation is controlled to assure a minimum dissolved oxygen concentration of at minimum 5% saturation.

Furthermore, the fermentation tank can be equipped with optical devices for monitoring levels of cell density, concentrations of metabolites and products regardless of their physio-chemical form. Formation and consumption of volatile compounds are monitored using gas analysis on the gas inlets to and gas outlets from the fermentation tank. All signals of monitored variables can be used for control purposes allowing for the variables to be maintained within predefined ranges or changed continuously according to predefined profile with respect to time. Alternatively, variables are controlled in response to signal changes from other monitored variable.

The desired product produced during the fermentation is present as soluble extracellular material or as intracellular material either in the form of soluble material or as insoluble material including aggregated material. Formation of product is either constitutive or induced and is dependent or independent of microbial growth. The fermentation process is carried out in tanks with a working volume ranging from 100 mL to 200.000 L. A fermentation process can be operated as a batch process, a fed-batch process, a repeated fed-batch process or a continuous process.

The medium used to culture the cells in the fermentation process may be any conventional medium suitable for growing the host cells, such as minimal or complex media containing appropriate supplements. Suitable media are available from commercial suppliers or may be prepared according to published recipes (e.g. in catalogues of the American Type Culture Collection). Thus the medium will contain at least one carbon source, one or several nitrogen sources, essential salts including salts of potassium, sodium, magnesium, phosphate, nitrate and sulphate, trace metals, water soluble vitamins, process aids including but not limited to protease inhibitors, stabilizers, ligands, antifoam agents and inducers. The medium may contain components which are partly precipitated or dispersed in the liquid medium at some operating conditions including sterilisation by heat. The medium can be made up by the mixing of several liquids and gaseous solutions. These solutions can be mixed prior to entering the fermentation tank or they are supplied to the fermentation tank as separate liquid streams added in a predefined ratio. The ratio between different liquid solutions of medium components can vary during the different stages of the fermentation process meaning that the overall composition of the medium may vary during the course of the fermentation.

A suitable fermentation medium may contain between 20 and 60 mM salts of mM $PO_4^{3-}$, between 50 and 70 mM $K^+$, between 20 and 35 mM $SO_4^{2-}$, between 4 and 6 mM $Na^+$, between 6 and 13 mM $Mg^{2+}$, between 0.5 and 1.5 mM $Mn^{2+}$, between 0.02 and 0.04 mM $Cu^{2+}$, between 0.1 and 0.3 mM $Fe^{2+}$, between 0.01 and 0.05 mM $Zn^{2+}$, trace amounts of Co, Mo and Ni added as part of a complex amino acid source, between 1 and 40 g/L of yeast extract, vitamins selected from m-inositol (between 100 and 250 mg/L), Ca-pantothenate (between 2 and 20 mg/L), thiamine, HCl (between 0.5 and 20 mg/L), pyridoxine (between 0.2 and 20 mg/L), niacin nicotinamide (between 2 and 7 mg/L), biotin (between 0.03 and 0.8 mg/L), and choline-dihydrogencitrate (between 0.1 and 0.2 mg/L), a ligand such as citric acid, $H_2O$ (between 0.5 and 7 g/L) and glucose as carbon source (between 50 and 200 g/L). Nitrogen is added continuously as either gaseous $NH_3$ or liquid $NH_4OH$ in an amount of between 400 and 1800 mM. Tap water is used as a natural source of calcium and $Cl^-$.

The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

After isolation from the culture broth the insulin or insulin analogue may be converted into e.g. acylated forms by acylation of in particular the &amino group of the B29Lys residue. Methods for acylation of insulins are well known in the art and disclosed in e.g. EP patents 792,290 and 894,095 and in U.S. Pat. Nos. 5,693,609, 5,646,242, 5,922,675, 5,750,497 and 6,011,007.

Example of acylated insulins are $N^{\epsilon B29}$-tetradecanoyl des (B30) human insulin, $N^{\epsilon B29}$-lithocholoyl-γ-glutamyl des (B30) human insulin, $N^{\epsilon B29}$—($N^{\alpha}$—($HOOC(CH_2)_{14}CO$)-γ-Glu) des(B30) human insulin or $N^{\epsilon B29}$—($N^{\alpha}$—($HOOC(CH_2)_{16}CO$)-γ-Glu) des(B30) human insulin.

With "desB30" or "B(1-29)" is meant a natural insulin B chain lacking the B30 amino acid residue, B(1-30) means the natural B chain of human insulin and "A(1-21)" means the natural insulin A chain. A18Q human insulin is an insulin analogue having a Gln in position A18 of the human insulin A-chain. B10E, A8H, A14E is an insulin analogue having a Glu in position B10, a His in position A8 and a Glu in position A14 respectively.

With "B1", "A1" etc. is meant the amino acid residue in position 1 in the B chain of insulin (counted from the N-terminal end) and the amino acid residue in position 1 in the A chain of insulin (counted from the N-terminal end), respectively. The amino acid residue in a specific position may also be denoted as e.g. $Phe^{B1}$ which means that the amino acid residue in position B1 is a phenylalanine residue.

With "C-peptide" is meant the peptide sequence linking the A- and B-peptide chains of the insulin molecule together including the cleavage sites at each end.

With "connecting peptide" is meant the peptide sequence between the two cleavage sites at each junction with the A- and B-chain respectively.

With "mature human insulin analogue" is meant an active two-chain insulin analogue with the same structural conformation as the natural human insulin molecule e.g. with disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$ but with certain mutations in one or more positions in the A and/or the B-chain compared to the natural amino acid residue in the corresponding position.

By "insulin analogue" as used herein is meant a polypeptide which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues. The insulin analogues will typically not comprise more than about 7 mutations, more typically not more than 5 and even more typically at the most 3 mutations compared to human insulin.

The insulin analogues may be such wherein position 28 of the B chain may be modified from the natural Pro residue to Asp, Lys, or Ile. Lys in position B29 may also be modified to Pro.

Also, Asn at position A21 may be modified to Ala, Gln, Glu, Gly, His, Ile, Leu, Met, Ser, Thr, Trp, Tyr or Val, in particular to Gly, Ala, Ser, or Thr and in particular to Gly. Furthermore, Asn at position B3 may be modified to Lys or Asp. Further examples of insulin analogues are des(B30) human insulin, insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Further insulin analogues are such wherein one or more of B26-B30 has been deleted.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by acylating a free amino group or a hydroxy group.

With "Kex2" is meant a subtilisin-like endoprotease that preferentially catalyzes cleavage after a sequence of two basic residues (lysine or arginine) (Rockwell, N C, Krysan, D J, Komiyama, T & Fuller, R S 2002 Precursor Processing by Kex2/Furin Proteases. Chem. Rev. 102: 4525-4548).

With "Kex1" is meant a serine carboxypeptidase that preferentially catalyzes removal of C-terminal lysyl and/or arginyl residues (Shilton B H, Thomas D Y, Cygler M 1997 Crystal structure of Kex1 deltap, a prohormone-processing carboxypeptidase from *Saccharomyces cerevisiae*. Biochemistry 36: 9002-9012).

With "Yps1" is meant an aspartyl protease that partially suppresses the pro-alpha-mating factor processing defect in yeast mutants that lack the natural pro-alpha-mating factor processing enzyme Kex2 (Egel-Mitani et al., Yeast 6, 1990, pp. 127-137).

With "correctly processed" is meant an enzymatic cleavage at the desired cleavage point giving the desired product with correct amino acid residue sequence.

"POT" is the *Schizosaccharomyces* pombe triose phosphate isomerase gene, and "TPI1" is the *S. cerevisiae* triose phosphate isomerase gene.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the host organism producing the protein.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase or lipase gene, or the *Rhizomucor miehei* lipase or protease gene, *Aspergillus* sp. amylase or glucoamylase, a gene encoding a *Rhizomucor miehei* lipase or protease. The signal peptide is preferably derived from a gene encoding *A. oryzae* TAKA amylase, *A. niger* neutral a-amylase, *A. niger* acid-stable amylase, or *A. niger* glucoamylase.

Useful signal peptides for yeast host cells are obtained from the genes for *Saccharomyces cerevisiae* a-factor and *Saccharomyces cerevisiae* invertase. A number of signal peptides which may be used with the DNA construct of the invention including yeast aspartic protease 3 (Yps1) signal peptide or any functional analogue (Egel-Mitani et al. (1990) YEAST 6:127-137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143-180, Cold Spring Harbor Laboratory, NY and U.S. Pat. No. 4,870,008, the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897) and the yeast BAR1 signal peptide (cf. WO 87/02670).

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498. WO 89/02463, WO 92/11378 and WO 98/32867.

The polynucleotide sequence of the invention may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or host cell and which carries a polynucleotide sequence encoding the insulin precursors of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In one embodiment, the recombinant expression vector is capable of replicating in yeast. Examples of sequences which enable the vector to replicate in yeast are the yeast plasmid 2 μm replication genes REP 1-3 and origin of replication.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

Selectable markers for use in a filamentous fungal host cell include amdS (acetamidase), argB (ornithine carbamoyltransferase), pyrG (orotidine-5'-phosphate decarboxylase) and trpC (anthranilate synthase.

Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase.

In a yeast host, useful promoters are the *Saccharomyces cerevisiae* MFα1, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419-434).

The procedures used to ligate the DNA sequences coding for the insulin precursor, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

It will be understood that the vector may be constructed either by first preparing a DNA construct containing the entire DNA sequence encoding the insulin precursors of the invention, and subsequently inserting this fragment into a suitable expression vector, or by sequentially inserting DNA fragments containing genetic information for the individual elements (such as the signal, pro-peptide, modified C-peptide, A and B chains) followed by ligation.

The present invention also relates to recombinant fungi cells, comprising a polynucleotide sequence encoding the insulin precursors of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication.

The host cell used in the present invention is a fungal cell. "Fungi" as used herein includes the *Ascomycota, Basidiomycota, Chytridiomycota,* and *Zygomycota* (as defined by Hawksworth et al., In, Ainsworth and Bisby's Dictionary of The Fungi, 8th edition, 1995, CAB International, University Press, Cambridge, UK) as well as the *Oomycota* (as cited in Hawksworth et al., 1995, supra, page 171) and all mitosporic fungi (Hawksworth et al., 1995, supra).

In one embodiment the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces* and *Saccharomyces*). The basidiosporogenous yeasts include the genera *Leucosporidim, Rhodosporidium, Sporidiobolus, Filobasidium,* and *Filobasidiella*. Yeast belonging to the Fungi Imperfecti are divided into two families, Sporobolomycetaceae (e.g., genera *Sorobolomyces* and *Bullera*) and Cryptococcaceae (e.g., genus *Candida*). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast Saccharomyces, Strathern et al., editors, 1981).

The yeast host cell may be selected from a cell of a species of *Candida, Kluyveromyces, Saccharomyces, Schizosaccharomyces, Pichia, Hansenula, Yarrowia*. In one embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Sacchoromyces uvarum, Pichia kluyveri, Yarrowia lipolytica, Candida utilis, Candida cacaoi,* and *Geotrichum fermentans*. Other useful yeast host cells are a *Kluyveromyces lactis, Kluyveromyces fragilis, Hansenula polymorpha, Pichia pastoris Yarrowia lipolytica, Schizosaccharomyces pombe, Ustilgo maylis, Candida maltose, Pichia guillermondii and *Pichia methanoliol* (cf. Gleeson et al., *J. Gen. Microbiol.* 132, 1986, pp. 3459-3465; U.S. Pat. No. 4,882,279 and U.S. Pat. No. 4,879,231).

In one embodiment the fungal host cell is a filamentous fungal cell. "Filamentous fungi" include all filamentous forms of the subdivision *Eumycota* and *Oomycota* (as defined by Hawksworth et al., 1995, supra). The filamentous fungi are characterized by a vegetative mycelium composed of chitin, cellulose, glucan, chitosan, mannan, and other complex polysaccharides. The filamentous fungal host cell may be chosen from the group consisting of *Acremonium, Aspergillus, Fusarium, Humicola, Mucor, Myceliophthora, Neurospora, Penicillium, Thielavia, Tolypocladium,* and *Trichoderma*

The expression "a codable amino acid" or "a codable amino acid residue" is used to indicate an amino acid or amino acid residue which can be coded for by a triplet ("codon") of nucleotides.

In the present context the three-letter or one-letter indications of the amino acids have been used in their conventional meaning as indicated in the following table. Unless indicated explicitly, the amino acids mentioned herein are L-amino acids. Further, the left and right ends of an amino acid sequence of a peptide are, respectively, the N- and C-termini unless otherwise specified.

Abbreviations for Amino Acids:

| Amino acid | Tree-letter code | One-letter code |
| --- | --- | --- |
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

By fermentation is meant an aseptic process used for propagating micro-organisms submerged into a liquid medium. The fermentation is preferably carried out in aseptic, stirred tanks with supply lines for addition of compressed, sterile gasses consisting of but not limited to air, oxygen and ammonia. A fermentation tank can contain devices/sensors for monitoring pH, temperature, pressure, agitation rate, dissolved oxygen level, liquid content, foam level, feed addition rates and rates of adding acid and base. Furthermore, the fermentation tank can be equipped with optical devises for monitoring levels of cell density, concentrations of metabolites and products regardless of their physio-chemical form. Formation and consumption of volatile compounds are monitored using gas analysis on the gas inlets to and gas outlets from the fermentation tank. All signals of monitored variables can be used for control purposes allowing for the variables to be maintained within predefined ranges or changed continuously according to predefined profile with respect to time. Alternatively, variables are controlled in response to signal changes from other monitored variable.

The desired product produced during the fermentation is present as soluble extracellular material or as intracellular material either in the form of soluble material or as insoluble material including aggregated material. Formation of product is either constitutive or induced and is dependent or independent of microbial growth. The fermentation process is carried out in tanks with a working volume ranging from 100 mL to 200.000 L. A fermentation process can be operated as a batch process, a fed-batch process, a repeated fed-batch process or a continuous process.

With a Batch process is meant a fermentation in which the sterile medium is contained within the fermentation tank before the micro-organisms are added to the tank. During the process acid, base, antifoam agent, inhibitors, stabilizers and inducers are added either automatically or manually. Acid and base are added either as liquid solutions or as gaseous components. These components can be added via one feed line or they can be supplied to the fermentation tank in separate lines. The fermentation tank content is only removed for purposes of analysis during the fermentation process. The entire content of the fermentation tank is harvested at the end of the fermentation process. However, for consecutive batch processes the content of the fermentation tank is only partly harvested and the fermentation tank is refilled with fresh, sterile medium allowing for another batch fermentation to take place.

A Fed-batch process is a fermentation in which only a part of the medium is filled into the fermentation tank before the micro-organisms are added. The remaining medium components or remaining amounts of already partly added medium components are supplied to the fermentation tank either as one pulse, as a series of discrete pulses or as a continuous flow added at constant or variable rate. A fed-batch process can be preceded by a batch process followed by the fed-batch operational mode. Medium components added to the fermentation tank during the process consist of but are not limited to growth limiting components, sparingly soluble components, volatile components or components with limited stability in liquid environment. The growth rate of the micro-organisms can be controlled through adjustments of the rate by which medium components are added to the fermentation tank. Acid, base, antifoam, inhibitors, stabilizers and inducer are added during the process either automatically or manually. Acid and base are added either as part of liquid solutions or as gaseous components. All components added during the fed-batch process are supplied via one feed line or they can be supplied to the fermentation tank in separate supply lines. During a fed-batch process the fermentation tank content is only removed for the purposes of analysis. The entire content of the fermentation tank is harvested at the end of the process.

A variant of the fed-batch process is the Repeated-Fed-batch process. A repeated-fed-batch fermentation is carried out similar to a fed-batch process but part of the fermentation tank content is removed at one or several instances during the process. Partial removal of fermentation tank content can be followed by addition of fresh medium. Addition of fresh medium can be followed by a batch process before resuming fed-batch process operation. The composition of fresh medium and the medium added during the fed-batch process are not necessarily identical.

By a Continuous process is meant a fermentation in which some of the medium is added to the tank before the micro-organisms are added and the fermentation started. Fresh medium containing all medium components necessary for growth together with inhibitors, inducers, antifoam, acid, base and components stabilizing the product are added continuously. These components can be added via one feed line or they can be supplied to the fermentation tank in separate supply lines in order to increase the stability of the used medium or improve its quality. Acid and base are added either as part of liquid solutions or as gaseous components. All components are added to the fermentation tank as a series of discrete pulses or as a continuous flow added at constant or variable rate. Harvest of the fermentation tank content is carried out continuously in order to maintain the content of the fermentation tank within a predefined range. Growth of the micro-organism can be controlled by the rate of medium addition to the fermentation tank as well as by adjustment of the fermentation tank content.

By a medium is meant a liquid solution containing at least one carbon source, one or several nitrogen sources, essential salts including salts of potassium, sodium, magnesium, phosphate, nitrate and sulphate, trace metals, water soluble vitamins, process aids including but not limited to protease inhibitors, stabilizers, ligands, antifoam agents and inducers. The medium may contain components which are partly precipitated or dispersed in the liquid medium at some operating conditions including sterilisation by heat. The medium can be made up by the mixing of several liquids and gaseous solutions. These solutions can be mixed prior to entering the fermentation tank or they are supplied to the fermentation tank as separate liquid streams added in a predefined ratio. The ratio between different liquid solutions of medium components can vary during the different stages of the fermentation process meaning that the overall composition of the medium may vary during the course of the fermentation. The table below contains a list of concentration ranges for different medium components. These concentrations are calculated as the total amount of an added medium component divided by the initial volume of medium in the fermentation tank. Media concentrations for continuous cultivations are included as the concentrations in medium entering the fermentation tank.

The following table is a review of the typical components of a fermentation medium.

| Main purpose | Component | Low level | High level |
|---|---|---|---|
| C-sources | Glucose | 0 | 500 g/L |
| | Sucrose | 0 | 500 g/L |
| | Maltose | 0 | 500 g/L |
| | Lactose | 0 | 300 g/L |
| | L-Malic acid | 0 | 200 g/L |
| | Maltodextrins | 0 | 600 g/L |
| | Ethanol | 0 | 500 g/L |
| | Methanol | 0 | 500 g/L |
| | Pectins | 0 | 40 g/L |
| | Fatty acids | 0 | 50 g/L |
| | PIT emulsions of oils | 0 | 20 g/L |
| | Triglycerides | 0 | 60 g/L |
| Inorganic P-source | Salts of orthophosphate | 4 mM | 100 mM |
| Minerals essential for growth | Salts of sulphate | 1 mM | 60 mM |
| | Salts of ammonium | 0 | 1800 mM |
| | Salts of magnesium | 0.5 mM | 20 mM |
| | Salts of potassium | 3 mM | 100 mM |
| | Salts of sodium | 0.2 | 500 mM |
| | Salts of calcium | 1 mM | 50 mM |
| Other N-sources | Ammonia | 0 | 1800 mM |
| | Urea | 0 | 900 mM |
| | Amino acids | 0 | 25 g/L |
| | Corn steep liquor | 0 | 100 g/L |
| | Yeast extract | 0 | 75 g/L |
| | Plant proteins | 0 | 50 g/L |
| | Hydrolyzed plant proteins | 0 | 30 g/L |
| Trace metals | Fe | 10 | 350 μM |
| | Zn | 10 | 300 μM |
| | Mn | 5 | 1500 μM |
| | Cu | 3 | 75 μM |
| | Mo | 0 | 1 μM |
| | $H_3BO_3$ | 0 | 60 μM |
| Vitamins | Biotin | 0.01 mg/L | 10 mg/L |
| | Pantothenate, Ca | 1 mg/L | 1000 mg/L |
| | Niacin | 1 mg/L | 200 mg/L |
| | Thiamin, HCl | 0.2 mg/L | 200 mg/L |
| | p-Aminobenzoic acid | 0 | 100 mg/L |
| | Choline dihydrogen citrate | 10 mg/L | 200 mg/L |
| | m-Inositol | 10 mg/L | 2000 mg/L |
| | Pyridoxine, HCl | 0.2 mg/L | 100 mg/L |
| | Folic acid | 0 | 50 μg/L |
| | Riboflavin | 0 | 200 mg/L |
| | Ascorbic acid | 0 | 1000 mg/L |
| Auxotrophy | Uridine/Uracil | 0 | 1000 mg/L |
| Process aids and ligands. | PPO | 0 | 1000 ppm |
| | PPO-PEO block copolymer | 0 | 5000 ppm |
| | Antifoam (silicone based) | 0 | 1000 ppm |
| | Antifoam (oil based) | 0 | 1000 ppm |
| | Citric acid | 0 | 1000 mg/L |
| | Trimethylglycin | 0 | 10.000 mg/L |
| | Imidazol | 0 | 10 mM |
| | EDTA | 0 | 100 μM |
| | L-histidin | 0 | 1000 mg/L |
| | Non-metabolizale analogous of carbon sources. | 0 | 200 mg/L |

Pharmaceutical compositions containing the insulin analogues of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Pharmaceutical compositions of the insulin analogues will contain usual adjuvants and additives and are preferably formulated as an aqueous solution. The aqueous medium is made isotonic, for example, with sodium chloride, sodium acetate or glycerol. Furthermore, the aqueous medium may contain zinc ions, buffers and preservatives. The pH value of the composition is adjusted to the desired value and may be between about 4 to about 8.5.

In one embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

The pharmaceutical composition will comprise usual adjuvants such one or more agents suitable for stabilization, preservation or isotonicity, for example, zinc ions, phenol, cresol, a parabene, sodium chloride, glycerol or mannitol.

The buffer used in the pharmaceutical may be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof.

The pharmaceutically acceptable preservative may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19th edition, 1995.

The isotonicity agent may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol(propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. The use of an isotonic agent in pharmaceutical compositions is well-known to the skilled person. For convenience reference is made to Remington: The Science and Practice of Pharmacy, 19th edition, 1995.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

General Procedures

All expressions plasmids are of the C-POT type, similar to those described in EP 171, 142. These are 2μ-based expression vectors characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator sequences. These sequences are similar to the corresponding sequences in plasmid pKFN1003 (described in WO 9010075).

Yeast transformants are prepared by transformation of the host strains S. cerevisiae strain MT663 or ME1719. The yeast strain MT663 (MATa/MATα pep4-3/pep4-3 HIS4/his4 Δtpi::LEU2/Δtpi::LEU2 Cir') was deposited in the Deutsche Sammlung von Mikroorganismen und Zellkulturen in connection with filing WO 92I11378 and was given the deposit number DSM 6278. S. cerevisiae strain ME1719 (MATa/α leu2/leu2 pep4-3/pep4-3 Δtpi::LEU2/Δtpi::LEU2 Δura3/Δura3 Δyps1::URA3/Δyps1::ura3 Cir+) is described in WO 98/01535.

MT663 or ME1719 are grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM $Na_2EDTA$ pH=8.0 and 6.7 mg|ml dithiotreitol. The suspension is incubated at 30° C. for 15 minutes, centrifuged and the cells resuspended in 10 ml of a solution containing 1.2 M sorbitol, 10 mM Na2EDTA. 0.1 M sodium citrate, pH 0 5.8, and 2 mg NovozymC3234. The suspension is incubated at 30° C. for 30 minutes, the cells are collected by centrifugation, washed in 10 ml of 1.2 M sorbitol and 10 ml of CAS (1.2 M sorbitol, 10 mM $CaCl_2$, 10 mM Tris HCl (Tris=Tris (hydroxymethyl)-aminomethane) pH=7.5) and resuspended in 2 ml of CAS. For transformation, 1 ml of CAS-suspended cells is mixed with approx. 0.1 mg of plasmid DNA and left at room temperature for 15 minutes. 1 ml of (20% polyethylene glycol 4000, 10 mM $CaCl_2$, 10 mM Tris HCl, pH=7.5) is added and the mixture left for a further 30 minutes at room temperature. The mixture is centrifuged and the pellet resuspended in 0.1 ml of SOS (1.2 M sorbitol, 33% v|v YPD, 6.7 mM $CaCl_2$) and incubated at 30° C. for 2 hours. The suspension is then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. is added and the suspension poured on top of plates containing the same agar-solidified, sorbitol containing medium.

Example 1

Construction of a Yeast Expression System for A18Q-Insulin

FIG. 1 shows a yeast plasmid called pSA50. The plasmid contains an expression cassette comprising an EcoRI-XbaI fragment inserted into the plasmid between the transcription-promoter and the transcription-terminator of the S. cerevisiae TPI gene. In plasmid pSA50 the EcoRI-XbaI fragment encodes a fusion product composed of the MFα1* pre-pro leader, a Lys-Arg cleavage site for the dibasic processing endopeptidase KEX2, and the insulin precursor B(1-30)-KRDGLGKR-(A1-21), A18Q.

A DNA fragment containing sequences encoding the insulin precursor B(1-30)-KRDGLGKR-(A1-21), A18Q was constructed as follows. 2.5 pmol of oligonucleotides ASA-SCI-2 (corresponding to sequence 1279-1358 in FIG. 2) and SCI-kex2-3 (corresponding to sequence 1425-1337 in FIG. 2—reverse primer) were mixed in a PCR reaction containing 10 μl 10× HighFidelity buffer, 2.5 mM dNTP, 1 μl HighFidelity polymerase and 76 μl $H_2O$. After one cycle (94° C. for 30 sec., 50° C. for 30 sec., 72° C. for 1 minute) 100 pmol of oligonucleotides ASA-SCI1 (corresponding to 1252-1301 in FIG. 2) and ASA-SCI-7 (corresponding to sequence 1464-1407-reverse primer) was added followed by 9 cycles as above. The resulting PCR fragment was purified using a PCR purification kit from Roche, digested with NcoI and XbaI and finally run on agarose gels and purified using GFX-PCR Gel Band Purification Kit (Amersham Biosciences #27-9602-01). The fragment was ligated to the NcoI-XbaI vector fragment from the C-POT type expression vector described above ("General procedures").

The expression plasmid was propagated in E. coli, grown in the presence of ampicillin and isolated using standard techniques (Sambrook et al., 1989). The plasmid DNA was checked for insert by appropriate restriction nucleases (e.g. EcoRI, NcoI, XbaI) and was shown by sequence analysis to contain the proper sequence of the insulin precursor B(1-30)-KRDGLGKR-(A1-21), A18Q (FIG. 2).

The plasmid pSA50 was transformed into S. cerevisiae strain MT663. Yeast transformants harbouring plasmid pSA50 were selected by glucose utilization as carbon source on YPD (1% yeast extract, 2% peptone, 2% glucose) agar (2%) plates and the resulting strain was named ySA63.

Example 2

Production of Human Insulin Analogues

Plasmids comprising DNA encoding certain human insulin analogues were prepared by a method corresponding to the method described in example 1. A S. cerevisiae strain was transformed with the plasmids and transformants were isolated as described in example 1.

All precursors for the insulin analogues had the C-peptide KRDGLGKR (SEQ ID NO:9).

The S. cerevisiae strain MT663 transformed with a plasmid for expression of insulin analogue was inoculated into 5 ml of a medium consisting of 5 g/L $(NH_4)_2SO_4$, 184 mg/L $(NH_4)_2HPO_4$, 2.88 g/L $KH_2PO_4$, 1.42 g/L $MgSO_4.7H_2O$, 1.28 g/L, $K_2SO_4$, 10.00 g/L succinic acid, 10.00 g/L casamino acids, 0.0112 g/L $FeSO_4.7H_2O$, 0.0086 g/L $MnSO_4.H_2O$, 0.0014 g/L $CuSO_4.5H_2O$, 0.00185 g/L $ZnSO_4.7H_2O$, 0.0129 g/L $CaCl2.2H_2O$, 0.071 g/L citric acid, 28.0 mg/L m-inositol, 14.0 mg/L choline chloride, 2.8 mg/L thiamine, 2.8 mg/L niacinamide, 2.1 mg/L Ca-pantothenic acid, 0.14 mg/L biotin, 0.14 mg/L folic acid, 40 g/L glucose. The cultivation was carried out at 30° C. for 3 days. After centrifugation the supernatant was removed for quantitative HPLC analysis by which method the concentration of secreted insulin analogue was measured. The identity of the insulin analogues were confirmed by LC/MS analysis.

The yields (mg/l) appear from the following table

| C-peptide | Insulin mutations | Human insulin or human insulin analogue + the desB30 product |
| --- | --- | --- |
| KRDGLGKR (SEQ ID NO: 9) | A18Q | 2.0 |
| KRDGLGKR (SEQ ID NO: 9) | none | <1 |
| KRDGLGKR (SEQ ID NO: 9) | B10E, A8H, A14E | 25.0 |
| KRDGLGKR (SEQ ID NO: 9) | B10E | 4.0 |

-continued

| C-peptide | Insulin mutations | Human insulin or human insulin analogue + the desB30 product |
|---|---|---|
| KRDGLGKR (SEQ ID NO: 9) | A8H | 2.0 |
| KRDGLGKR (SEQ ID NO: 9) | A14E | 22.0 |

Example 3

Fed-Batch Fermentation

S. cerevisiae strain ySA63 expressing B(1-30)-KRDG-LGKR-(A1-21), A18Q inoculated into a medium consisting of yeast extract (Difco): 20 g/L and peptone (Bacto): 10 g/L and 60 g/L glucose and 0.1 mL of an antifoam agent (a PEO/PPO block copolymer). The medium pH is adjusted to 6.5-6.6 prior to heat sterilisation. The glucose is sterilized separately and added to the remaining sterile components.

200 mL of culture (in a 500 mL Erlenmeyer flask) is incubated in an orbital shaker at 30° C. and 250 rpm for 16-30 hours.

50 mL of shake flask culture is transferred to a fermentor containing 1.2 L of growth medium consisting of: 50 g/L of liquid yeast extract (50% dry matter), 3.6 g/L $KH_2PO_4$, 2.3 g/L $K_2SO_4$, 1.5 g/L $MgSO_4 \cdot 7H_2O$, 0.064 g/K $FeSO_4 \cdot 7H_2O$, 0.016 g/L $MnSO_4 \cdot H_2O$, 0.011 g/L $CuSO_4 \cdot 5H_2O$, 0.016 g/L $ZnSO_4 \cdot 7H_2O$, 0.8 g/L citric acid, 2 g/L m-inositol, 0.2 g/L choline chloride, 0.2 g/L thiamine, HCl, 0.1 g/L pyridoxine, HCl, 0.2 g/L niacinamide, 1 g/L Ca-pantothenic acid, 0.005 g/L biotin, 0.05 g/L p-aminobenzoic acid, 0.66 mL/L of antifoam agent (a PEO/PPO block copolymer) and 21 g/L glucose. All components expect glucose are heat sterilized. The glucose is sterilized separately and added to the fermentor.

Figure 3:
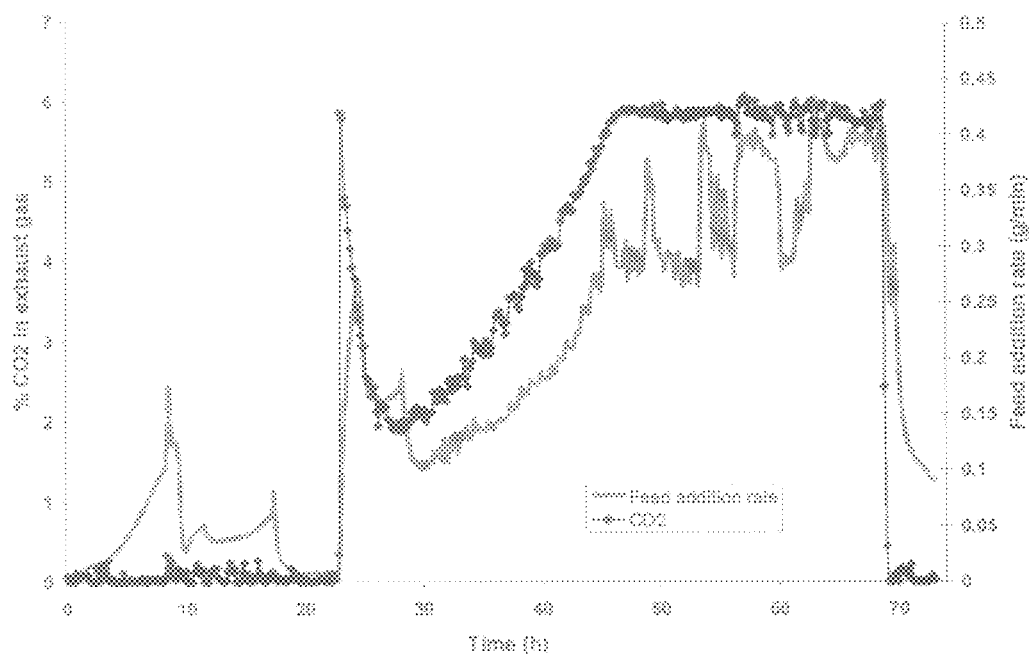
FIG. 3 discloses time profiles for the feed addition rate (g feed/min) to a fermentor using a starting volume of 1.25 L. Also shown is the carbon dioxide concentration in the exhaust gas from the fermentor as a function of time and FIG. 4 discloses time profiles for the optical density measured at 600 nm and the calculated concentration of insulin per L fermentation broth (including desB30 insulin).

The cultivation is carried out at 30° C. using a pH set point of 5.9 and an aeration rate of 1 vvm. The medium pH is maintained at the setpoint through addition of $NH_4OH$. Dissolved oxygen is monitored together with the exhaust gas composition (oxygen, carbon dioxide and ethanol). The fermentation process is initiated with a batch growth phase lasting 23 hours during which the glucose is consumed fermentatively followed by aerobic batch growth on the previously formed ethanol. Subsequently, when the ethanol level in the exhaust gas starts to decrease addition of a feed solution consisting of 50% (w/w) glucose is initiated. The feed addition rate follows the profile shown in FIG. 3 including manual adjustments in order to keep the ethanol level in the exhaust gas below 250 ppm.

During the process growth is monitored by measurements of the optical density at 600 nm on diluted fermentation samples. The concentration of insulin is quantified by HPLC on samples diluted 1:1 on a volume basis with acidic ethanol (552 g ethanol, 340 g deionized water and 5 mL of concentrated sulphuric acid) and centrifuged at 3000-5000×g. When calculating the concentration of insulin per L fermentation broth corrections for the volume occupied by the yeast cells is included assuming a rhombic packaging of the cells in the precipitate. The reported concentration of insulin includes intact insulin and desB30 insulin.

The addition of glucose solution is stopped after 69 hours whereas the fermentation is continued for another 4 hours before harvest of the product.

Figure 4:
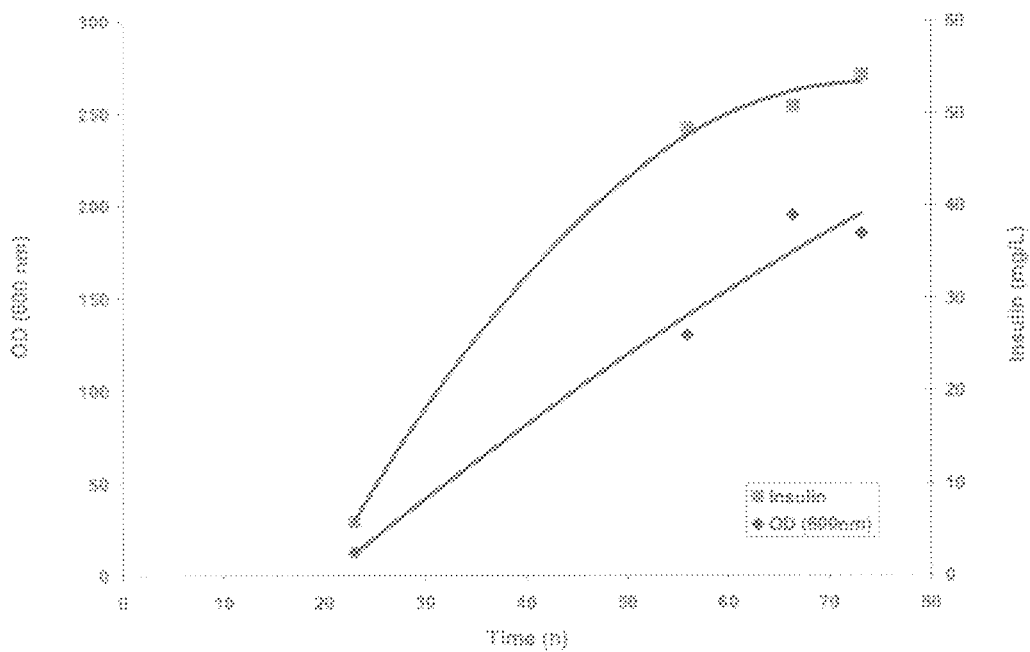

Optical density and insulin concentration versus time are plotted in FIG. 4 showing a final insulin concentration of 37 mg/L fermentation broth.

The invention claimed is:

1. A method for making mature human insulin analogues by culturing a fungi cell comprising a DNA vector encoding a precursor for a human insulin analogue, wherein the said precursor comprises a connecting peptide flanked with cleavage sites at both junctions to the A- and B-chain of the insulin peptide, respectively, said cleavage sites being cleaved within the fungi cell allowing the cell to secrete the correctly processed mature, two chain human insulin analogue into the culture media, wherein the insulin analogue has Glu at position A14, and a mutation in at least one of the positions A8, B10, and A18 in the human insulin A- and/or the B-chain selected from the group consisting of Asp, Glu, His, Gln and Arg.

2. The method according to claim 1, wherein the cleavage sites are Kex2 cleavage sites.

3. The method according to claim 1, wherein the amino acid residue in the connecting peptide in the position penultimate to the cleavage site next to the A-chain is selected from the group consisting of Leu, Ile, Tyr, Arg, Lys, His, Pro, Met, Val, Ala and Phe.

4. The method according to claim 3, wherein the amino acid residue is selected from the group consisting of Leu and Ile.

5. The method according to claim 1, wherein the connecting peptide has a size of 3-35, 3-34, 3-33, 3-31, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5 or 3-4 amino acid residues.

6. The method according to claim 1, wherein the insulin analogue is B10Glu, A8His, and A14Glu human insulin.

7. The method according to claim 1, wherein the fungi cell is capable of secreting at least about 20 to about 50 mg/liter correctly processed mature two chain human insulin analogue to the culture media.

8. The method according to claim 1, wherein the fungi cell is capable of secreting at least about 20 to about 80 mg/liter correctly processed mature two chain human insulin analogue to the culture media.

9. The method according to claim 1, wherein the fungi cell is capable of secreting at least about 100 mg/liter correctly processed mature two chain human insulin analogue to the culture media.

10. The method according to claim 1, wherein the fungi cell is a yeast cell.

11. The method according to claim 1, wherein the human insulin precursor analogue has the amino acid sequence

B(1-30)-X-X-Z-Y-Y-A(1-21)

where B(1-30) is the B-chain of human insulin or an analogue thereof, A(1-21) is the human insulin A-chain or an analogue thereof, each X and each Y independently of each other are Lys or Arg or a Yps1 site and Z is a peptide sequence with from 1 to about 35 amino acid residues, with the proviso that at least one of the natural amino acid residues in the human insulin A- and/or the B-chain is mutated to another amino acid residue.

12. The method according to claim 11, wherein Z is of the size 3-35, 3-34, 3-33, 3-31, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5 or 3-4 amino acid residues.

13. The method according to claim 11, wherein X-X and Y-Y are both a Kex2 site.

14. An isolated DNA encoding an insulin precursor with the amino acid sequence

B(1-30)-X-X-Z-Y-Y-A(1-21)

where B(1-30) is the B-chain of human insulin or an analogue thereof, A(1-21) is the human insulin A-chain or an analogue thereof, each X and each Y independently of each other are Lys or Arg or a Yps1 site and Z is a peptide with from 1 to about 35 amino acid residues, with the proviso that at least one of the natural amino acid residues in the human insulin A- and/or the B-chain is mutated to another amino acid residue, wherein the insulin analogue has Glu at position A14, and a mutation in at least one of the positions A8, B10, and A18 in the human insulin A- and/or the B-chain, selected from the group consisting of Asp, Glu, His, Gln and Arg.

15. An expression vector comprising a DNA according to claim 14.

16. A yeast cell transformed with the vector according to claim 15.

\* \* \* \* \*

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Arg Arg Glu Ala Glu Asn Leu Gln Lys Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Arg Arg Glu Ala Pro Leu Gln Lys Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic
```

<400> SEQUENCE: 3

Arg Arg Glu Ala Leu Gln Lys Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Lys Arg Glu Ala Leu Gln Lys Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Arg Arg Leu Gln Lys Arg
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic

<400> SEQUENCE: 6

Lys Arg Glu Gln Lys Leu Ile Ser Glu Glu Ala Leu Val Asp Lys Arg
1               5                   10                  15

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Asp Gly Leu Gly
1

<210> SEQ ID NO 8
<211> LENGTH: 204
<212> TYPE: DNA
<213> ORGANISM: Homo sapiens
<220> FEATURE:
<221> NAME/KEY: misc_feature
<222> LOCATION: (1)..(193)
<223> OTHER INFORMATION: this is a coding region
<220> FEATURE:
<221> NAME/KEY: misc_feature
<222> LOCATION: (2)..(193)
<223> OTHER INFORMATION: this is a coding region

<400> SEQUENCE: 8
atccatggct aagagattcg ttaaccaaca cttgtgcggt tcccacttgg ttgaagcttt      60
gtacttggtt tgcggtgaaa gaggtttctt ctacactcct aagactaaga gagacggttt     120

```
gggtaagaga ggtattgtcg agcaatgctg tacatccatc tgctccttgt accaattgga      180
acaatactgc aactagactc taga                                             204
```

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

```
Lys Arg Asp Gly Leu Gly Lys Arg
1               5
```

<210> SEQ ID NO 10
<211> LENGTH: 65
<212> TYPE: PRT
<213> ORGANISM: Homo sapiens

<400> SEQUENCE: 10

```
Ser Met Ala Lys Arg Phe Val Asn Gln His Leu Cys Gly Ser His Leu
1               5                   10                  15

Val Gly Ala Leu Tyr Leu Val Cys Gly Glu Arg Gly Phe Phe Tyr Thr
            20                  25                  30

Pro Lys Thr Lys Arg Asp Gly Leu Gly Lys Arg Gly Ile Val Glu Gln
        35                  40                  45

Cys Cys Thr Ser Ile Cys Ser Leu Tyr Gln Leu Glu Gln Tyr Tyr Cys
    50                  55                  60

Asn
65
```